United States Patent
Hayashi

(10) Patent No.: US 10,612,052 B2
(45) Date of Patent: Apr. 7, 2020

(54) METHOD OF MANUFACTURING MICROBIALLY PRODUCED PLASTIC AND MICROBIALLY PRODUCED PLASTIC

(71) Applicant: KANEKA CORPORATION, Osaka-shi (JP)

(72) Inventor: Asuka Hayashi, Takasago (JP)

(73) Assignee: KANEKA CORPORATION, Osaka-shi (JP)

(*) Notice: Subject to any disclaimer, the term of this patent is extended or adjusted under 35 U.S.C. 154(b) by 0 days.

(21) Appl. No.: 15/568,572

(22) PCT Filed: Apr. 22, 2016

(86) PCT No.: PCT/JP2016/002158
§ 371 (c)(1),
(2) Date: Oct. 23, 2017

(87) PCT Pub. No.: WO2016/170797
PCT Pub. Date: Oct. 27, 2016

(65) Prior Publication Data
US 2018/0087076 A1  Mar. 29, 2018

(30) Foreign Application Priority Data
Apr. 24, 2015  (JP) ................. 2015-089483

(51) Int. Cl.
| | |
|---|---|
| *C12P 7/62* | (2006.01) |
| *C08L 101/16* | (2006.01) |
| *C08G 63/06* | (2006.01) |
| *C11B 5/00* | (2006.01) |

(52) U.S. Cl.
CPC .............. *C12P 7/625* (2013.01); *C08G 63/06* (2013.01); *C08L 101/16* (2013.01); *C11B 5/0021* (2013.01); *C12P 7/62* (2013.01)

(58) Field of Classification Search
None
See application file for complete search history.

(56) References Cited

U.S. PATENT DOCUMENTS 5,627,276 A   5/1997   Greer

FOREIGN PATENT DOCUMENTS

| EP | 0028488 A1 * | 5/1981 | ............ C11B 3/08 |
| JP | 8-502415 A | 3/1996 | |
| JP | 2012-115145 A | 6/2012 | |
| WO | WO-2014042076 A1 * | 3/2014 | ............ C12P 7/625 |

OTHER PUBLICATIONS

Machine translation of WO 2014042076. Retrived from https://worldwide.espacenet.com/publicationDetails/description?CC=WO&NR=2014042076A1&KC=A1&FT=D&ND=3&date=20140320&DB=&locale=en_EP# on Jul. 3, 2019.*
International Search Report dated Jul. 5, 2016 in PCT/JP2016/002158 filed Apr. 22, 2016.

* cited by examiner

*Primary Examiner* — Yong D Pak
(74) *Attorney, Agent, or Firm* — Oblon, McClelland, Maier & Neustadt, L.L.P.

(57) ABSTRACT

Provided is a method of manufacturing a microbially produced plastic having low coloration, good tone, and low odor, based on a simple, low-cost method that is suitable for industrial production. The method of manufacturing the microbially produced plastic is characterized in that a step (a) and a step (b), described below, are included: step (a) is a step of applying heat treatment to fat containing hydrogen peroxide, and step (b) is a step of culturing microbes in a culturing liquid containing the fat that has been subjected to the heat treatment in the step (a).

10 Claims, No Drawings

METHOD OF MANUFACTURING MICROBIALLY PRODUCED PLASTIC AND MICROBIALLY PRODUCED PLASTIC

TECHNICAL FIELD

The present invention relates to a method of manufacturing a microbially produced plastic and a microbially produced plastic.

BACKGROUND ART

Microbially produced plastics, particularly a polyhydroxyalkanoate (hereinafter sometimes referred to as PHA) is a thermoplastic polyester which is produced and accumulated as an energy storage substance in cells of many microbial species. PHA produced by microbes using natural organic acids and fats as a carbon source is completely biodegraded by microbes in the soil and water and is taken into the natural carbon cycle process, so that PHA is an environmentally compatible plastic material with almost no adverse effect on the ecosystem. In recent years, synthetic plastics have become a serious social problem from the viewpoints of environmental pollution, waste disposal, and petroleum resources, and PHA has attracted attention as an environmentally friendly green plastic and its practical application has been in great demand. Also in the medical field, it is thought that PHA can be used as a biocompatible plastic such as an implant material which is not required for collection, a drug carrier and so on. Thus, PHA is expected to be put into practical use.

However, there is a problem that PHA produced by microbes is colored during the production thereof, such as during the culturing process. Patent Literature 1 (PTL 1) describes a method in which an aqueous suspension of a microbe cell containing PHA produced by a microbe is subjected to enzymatic treatment, then an alkali and a surfactant are added, and physical crushing treatment is carried out at a relatively low temperature, thereby to obtain a PHA having a yellowness index (YI value) of 15.0 or less. However, there is room for improvement in terms of processability, because treatment conditions of treatment temperatures, etc., as well as the type and amount of additives used in the treatment are limited in order to prevent the molecular weight of PHA from decreasing. Furthermore, this method was difficult to put into practical use because the method requires a large amount of agents and large-scale facilities for improving the color tone of PHA.

CITATION LIST

Patent Literature

PTL 1: JP-A-2012-115145

SUMMARY OF INVENTION

Technical Problem

An object of the present invention is to provide a method of manufacturing a microbially produced plastic having low coloration, good color tone, and low odor, based on a simple, low-cost method that is suitable for industrial production.

Solution to Problem

As a result of intensive studies in view of the above problems, the present inventors have completed the present invention. That is, the present invention provides a method of manufacturing a microbially produced plastic according to the following [1] to [9] and a microbially produced plastic according to the following [10].

[1] A method of manufacturing a microbially produced plastic, including the following steps (a) and (b):
(a): a step of applying heat treatment to fat containing hydrogen peroxide, and
(b): a step of culturing microbes in a culturing liquid containing the fat that has been subjected to the heat treatment in the step (a).
[2] The method of manufacturing a microbially produced plastic according to [1], wherein the heat treatment is performed at a temperature of 50° C. or more and less than 150° C. in the step (a).
[3] The method of manufacturing a microbially produced plastic according to [1] or [2], wherein the fat contains a plant-derived fat.
[4] The method of manufacturing a microbially produced plastic according to [1] or [2], wherein the fat contains a residual oil.
[5] The method of manufacturing a microbially produced plastic according to [1] or [2], wherein the fat contains a palm-derived fat.
[6] The method of manufacturing a microbially produced plastic according to any one of [1] to [5], including a step (c) of taking out a plastic component from the microbes cultured in the step (b).
[7] The method of manufacturing a microbially produced plastic according to any one of [1] to [6], including a step (d) of emulsifying the fat by adding a surfactant to the fat that has been heat-treated in the step (a).
[8] The method of manufacturing a microbially produced plastic according to any one of [1] to [6], including a step (d') of emulsifying the fat by adding a surfactant and sodium hydroxide to the fat that has been heat-treated in the step (a).
[9] The method of manufacturing a microbially produced plastic according to any one of [1] to [8], wherein the microbially produced plastic is a polyhydroxyalkanoate.
[10] A microbially produced plastic, which is manufactured by the manufacturing method according to any one of [1] to [9].

Advantageous Effects of Invention

According to the manufacturing method of the present invention, it is possible to manufacture a microbially produced plastic, by a simple and low-cost method suitable for industrial production, with low coloration, good color tone, and low odor.

DESCRIPTION OF EMBODIMENTS

Hereinafter, an example of a preferred embodiment will be specifically described, but the present invention is not limited thereto.

The method of manufacturing a microbially produced plastic includes the following steps (a) and (b):
(a): a step of applying heat treatment to fat containing hydrogen peroxide, and
(b): a step of culturing microbes in a culturing liquid containing the fat that has been subjected to the heat treatment in the step (a).

The inventor of the present invention found that the cause of coloring of the microbially produced plastic is ubiquinones, particularly ubiquinone-8, which is formed at the time of plastic production by microbes. The method of manufacturing a microbially produced plastic of the present invention is to manufacture a plastic having low coloration and good color tone by suppressing the production amount of ubiquinone-8 during microbial culturing based on a simple and low-cost method.

Each step will be described in detail below.

[(a) Heat Treatment Step]

The step (a) is a step of applying heat treatment to fat containing hydrogen peroxide. The heating temperature in the heating step is not particularly limited as long as fat capable of suppressing the formation of ubiquinone-8 in the culturing liquid can be obtained, but the lower limit of the treatment temperature is preferably 50° C. or higher, more preferably 60° C. or higher, particularly preferably 70° C. or higher, from the viewpoint of formation of ubiquinone-8 being suppressed to easily obtain a plastic having low coloration and a low YI value, as well as from the viewpoint of easiness of obtaining fat having effects such as low coloration and deodorization. Also, in view of easily suppressing coloration due to decomposition of the fat and excessively high temperature, the upper limit of the treatment temperature of the fat is preferably less than 150° C., more preferably less than 130° C., and particularly preferably less than 120° C. Treatment of the fat in the above temperature range more suppresses the formation of ubiquinone-8, resulting in obtaining a plastic having low coloration.

The time of the heat treatment is not particularly limited as long as a fat capable of suppressing the formation of ubiquinone-8 can be obtained, but from the viewpoint that low coloration of the fat and deodorization effect can be easily obtained, the lower limit is preferably 0.5 hours or more, more preferably 1.5 hours or more, and still more preferably 2.0 hours or more. In addition, the upper limit of the heat treatment time is preferably 6 hours or less, more preferably 5 hours or less, from the viewpoint of ensuring productivity and easily suppressing coloration in the fat.

During the heat treatment, it is preferable to stir the fat containing hydrogen peroxide. The stirring method is not particularly limited as long as the fat and hydrogen peroxide can be uniformly mixed, but as a method of easily making the droplets finely and uniformly, a method of rotating turbine blades at a high rotation speed to mix the fat and hydrogen peroxide can be preferably used.

(Fat)

Fats are not particularly limited as long as they can culture microbes, and can be used regardless of the content of saturated fatty acids or unsaturated fatty acids. Specific examples of the fats that can be used include animal-derived fats such as beef tallow, bone oil, lard, chicken oil, whale oil, sheep fat, goat fat, horse oil, milk fat, sebum, and fish oil; plant-derived fats such as palm-derived fats (also called *Elaeis guineensis*) (e.g. palm oil, palm kernel oil, and palm olefin oil), coconut palm oil, corn oil, olive oil, Japanese hornwort seed oil, cottonseed oil, castor oil, soybean oil, rapeseed oil, sunflower oil, rice oil and safflower oil, or residual oils of these fats. Among the residual oils, it is possible to use a dark oil containing fatty acids and the like, which is generated in the deacidification step particularly at the time of refining fats.

The term "residual oil" as used herein means a remaining portion obtained in a distillation step of refining the fat, including the fat remaining in the distillation vessel after distillation and excluding the target portion generated by refining the fat, and the residual oil is a component with a higher color tone than the color tone of the distillation component (fat as product). Generally, the residual oil is not suitable for manufacturing a microbially produced plastic because it is strongly colored and have a strong odor, and thus such residual oil is not used. However, according to the manufacturing method of the present invention, even if a residual oil is used, a microbially produced plastic which has low coloration and low odor and which can withstand practical use can be manufactured.

The term "dark oil" refers to fat mainly composed of a fatty acid obtained by sulfuric acid decomposition of soda oil residue generated in a deacidification step at the time of refining the fat among residual oils. The type of the fats may be of animal origin or plant origin.

Among the above fats, from the viewpoint of availability, it is preferable to use plant-derived fats. From the viewpoint of cost and availability, it is preferable to use palm-derived fats such as palm oil and palm kernel oil. Since waste materials and non-edible materials are used, a residual oil is preferable in terms of environmental load and cost, though undesirable in terms of color tone and odor. From the viewpoint of availability, among residual oils, it is particularly preferable to use a residual oil of palm-derived fats such as palm kernel oil.

(Hydrogen Peroxide)

Hydrogen peroxide is not limited as long as it can suppress the formation of ubiquinone-8, and can be preferably used in a gaseous form or in a liquid form dissolved in a solvent such as water or an organic solvent, but it is more preferable to use hydrogen peroxide water in which hydrogen peroxide is mixed with water because hydrogen peroxide is easy to uniformly mix with fats.

In the case of using hydrogen peroxide water, the concentration of hydrogen peroxide in the hydrogen peroxide water is preferably 1% by weight or more, more preferably 5% by weight, particularly preferably 10% by weight or more in view of suppression of the formation of ubiquinone-8 and superiority in color tone reduction effect. The upper limit of the concentration of hydrogen peroxide in the hydrogen peroxide water is preferably 70% by weight or less, more preferably 65% by weight, and particularly preferably 60% by weight, from the viewpoints of availability and handleability.

Although it is preferable that the concentration of hydrogen peroxide water added to the fat is high, the lower limit is preferably 0.01% by weight or more, more preferably 0.1% by weight or more, particularly preferably 1% by weight or more, from the viewpoint of easily obtaining a color tone reduction effect of the fat and finally obtained microbially produced plastic. In addition, the upper limit of the concentration to be added is preferably 90% by weight or less, more preferably 85% by weight or less, and particularly preferably 80% by weight or less, from the viewpoint of easily suppressing the decomposition of the fat.

It is preferable to add a hydroxide salt or a carbonate of an alkali metal, such as sodium hydroxide, potassium hydroxide, calcium hydroxide, sodium carbonate, and potassium carbonate so that the formation of ubiquinone-8 in the fat is more suppressed when hydrogen peroxide is added. Particularly, when the step (d) is included as a subsequent step, it is preferable to use a hydroxide salt of an alkali metal from the viewpoint that the amount of the surfactant to be used can be suppressed.

In the case of using a hydroxide salt or a carbonate of an alkali metal, the lower limit of the concentration to be added is preferably 0.01% by weight or more, more preferably 0.05% by weight or more, and particularly preferably 0.1% by weight or more, with respect to the amount of the hydrogen peroxide water in terms of easily obtaining a color tone reduction effect of the finally produced microbially produced plastic. In addition, the upper limit of the concentration to be added is preferably 5% by weight or less, more preferably 4.5% by weight or less, particularly preferably 4.0% by weight or less, from the viewpoint of easily suppressing the decrease in the molecular weight of the fat. Hereinafter, one embodiment of the method of manufacturing the biodegradable plastic of the present invention will be described in detail, but the manufacturing method of the present invention is not limited thereto.

[(b) Culturing Step]

The step (b) is a step of culturing a microbe in a culturing liquid containing the fat that has been heat-treated in the step (a). In the culturing step, the method of culturing microbes is not particularly limited, but the method described in, for example, JP-A-05-93049 and the like can be preferably used.

(Culturing Liquid)

A culturing liquid can be prepared using a medium having a known composition as described in WO 2008/010296. The culturing liquid contains fat containing hydrogen peroxide, the fat having been heat-treated in the step (a), wherein the lower limit of the content of the fat in the culturing liquid is preferably 0.01% by weight or more, more preferably 0.05% by weight or more, most preferably 0.1% by weight or more. This lower limit is set for preventing a microbe from stopping the growth or for preventing decrease of the plastic accumulated in the microbe due to depletion of the fat during culturing. The upper limit of the content of the fat in the culturing liquid is preferably 5% by weight or less, more preferably 1% by weight or less, most preferably 0.5% by weight or less. This upper limit is set for preventing a microbe from stopping the growth due to substrate inhibition or foaming troubles during culturing.

(Microbes)

The microbes that produce the microbially produced PHA are not particularly limited as long as they have the ability to produce PHAs. For example, *Bacillus megaterium* is a first poly(3-hydroxybutyrate) (hereinafter, abbreviated as "PHB")-producing microbe discovered in 1925, and natural microbes such as *Cupriavidus necator* (formerly classified as *Alcaligenes eutrophus, Ralstonia eutropha*) and *Alcaligenes latus* are known as other PHB-producing microbes. These microbes accumulate PHB in their cells.

Further, known microbes that produce copolymers of hydroxybutyrate and another hydroxyalkanoate are, for example, *Aeromonas caviae* that produces PHBV and PHBH and *Alcaligenes eutrophus* that produces P3HB4HB. Particularly, a preferred PHBH-producing microbe is, for example, *Alcaligenes eutrophus* AC32, FERM BP-6038 (T. Fukui, Y. Doi, J. Bateriol., 179, p. 4821-4830 (1997)) produced by introducing a PHA synthase gene to improve PHBH productivity. These microbes are cultured under appropriate conditions, and the thus obtained cells having PHBH accumulated therein are used. Other than the above microbes, genetically-modified microbes may also be used which are produced by introducing various PHA synthesis-related genes in accordance with the desired type of PHAs to be produced. In this case, it is preferable to optimize the culture conditions including the culture medium components in accordance with the microbes.

[(c) Refining Step]

In addition to the above steps (a) and (b), it is preferable to include a step (c) of taking out a plastic component from the microbes cultured in the step (b). The step of taking out the plastic component from the microbes in this way is also referred to as a refining step. This makes it possible to increase the purity of the target microbially produced plastic.

The method of taking out the plastic component from the microbes is not particularly limited, and a known method can be used. For example, the method described in JP-A-2012-115145 can be preferably used.

[(d) Emulsification Step]

In addition to the above steps (a) and (b), it is preferable to include a step (d) of emulsifying the fat by adding a surfactant to the fat that has been heat-treated in the step (a). It is more preferable to include a step (d') of emulsifying the fat by adding a surfactant and an alkali to the fat that has been heat-treated in the step (a). Thus, the step of emulsifying the fat is also referred to as an emulsification step.

The emulsification step (d) or (d') is included between the heat treatment step (a) and the culturing step (b).

A method of including a surfactant in the heat-treated fat in the step (a) will be described. The surfactant can be dissolved in water and used as an emulsion. Specifically, as such an inclusion method, there are exemplified, a method in which the emulsion is added to the fat obtained in the step (a) and then the mixture is vigorously stirred by an emulsifying machine, thereby giving an emulsion; or a method in which the fat obtained in the step (a) is added to the emulsion and then the mixture is vigorously stirred by an emulsifying machine, thereby giving an emulsion. Culturing of microbes can be further promoted by vigorously stirring and uniformly emulsifying them. Here, the emulsifying machine is not particularly limited as long as it is an apparatus capable of uniformly emulsifying fat and water, but examples thereof include a high pressure homogenizer, an ultrasonic crusher, an emulsification disperser, a bead mill, and the like.

Examples of the surfactant used in the step (d) or (d') include an anionic surfactant, a cationic surfactant, an amphoteric surfactant, and a nonionic surfactant.

Examples of the anionic surfactant include fatty acid soaps (for example, sodium laurate, sodium palmitate, etc.); higher alkyl sulfate salts (for example, sodium lauryl sulfate, potassium lauryl sulfate, etc.); alkyl ether sulfate esters (for example, triethanolamine POE-lauryl sulfate, etc.); phosphate ester salts (for example, POE oleyl ether sodium phosphate, POE stearyl ether phosphate, etc.); sulfosuccinate salts (for example, sodium di-2-ethylhexyl sulfosuccinate, sodium monolauroylmonoethanolamide polyoxyethylene sulfosuccinate, sodium laurylpolypropylene glycol sulfosuccinate, etc.); alkylbenzene sulfonate salts (for example, sodium linear dodecylbenzenesulfonate, triethanolamine linear dodecylbenzenesulfonate, linear dodecylbenzenesulfonic acid, etc.); higher fatty acid ester sulfate salts (for example, hardened coconut oil fatty acid glycerin sulfate sodium, etc.); N-acylglutamate salts (for example, monosodium N-lauroylglutamate, disodium N-stearoylglutamate, monosodium N-myristoyl-L-glutamate, etc.); sulfated oils (for example, Turkey red oil, etc.); POE alkyl ether carboxylic acids; POE alkyl allyl ether carboxylate salts; α-olefin sulfonate salts; higher fatty acid ester sulfonate salts; secondary alcohol sulfate ester salts; higher fatty acid alkylolamide sulfate ester salts; sodium lauroyl monoethanolamide succinate; ditriethanolamine N-palmitoylaspartate; sodium caseinate, sodium hexametaphosphate, and the like.

Examples of the cationic surfactant include quaternary ammonium salts (for example, tetramethylammonium chloride, tetramethylammonium hydroxide, tetrabutylammonium chloride, etc.); alkylamine salts (for example, monomethylamine hydrochloride, dimethylamine hydrochloride, trimethylamine hydrochloride, etc.); substances having a pyridine ring (for example, butylpyridinium chloride, dodecylpyridinium chloride, cetylpyridinium chloride, etc.), and the like.

Examples of the lipophilic non-ionic surfactant include fatty acid monoglycerides, sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexanoate, diglycerolsorbitan tetra-2-ethylhexanoate, etc.); glycerol polyglycerol fatty acids (for example, mono-cottonseed-fatty acid glyceryl ester, glyceryl monoerucate, glyceryl sesquioleate, glyceryl monostearate, glyceryl α,α'-oleate pyroglutamate, glyceryl monostearate malate, etc.); propylene glycol fatty acid esters (for example, propylene glycol monostearate, etc.); hardened castor oil derivatives; glycerol alkyl ethers; and the like.

Examples of the hydrophilic non-ionic surfactant include POE sorbitan fatty acid esters (for example, POE sorbitan monooleate, POE sorbitan monostearate, POE sorbitan monooleate, POE sorbitan tetraoleate, etc.); POE sorbitol fatty acid esters (for example, POE sorbitol monolaurate, POE sorbitol monooleate, POE sorbitol pentaoleate, POE sorbitol monostearate, etc.); POE glycerol fatty acid esters (for example, POE glycerol monostearate, POE glycerol monoisostearate, POE glycerol triisostearate, etc.); POE fatty acid esters (for example, POE distearate, POE monodioleate, ethylene glycol distearate, etc.); POE alkyl ethers (for example, POE lauryl ether, POE oleyl ether, POE stearyl ether, POE behenyl ether, POE-2-octyldodecyl ether, POE cholestanol ether, etc.); Pluronic type surfactants (for example, Pluronic, etc.); POE/POP alkyl ethers (for example, POE/POP cetyl ether, POE/POP-2-decyl tetradecyl ether, POE/POP monobutyl ether, POE/POP hydrogenated lanolin, POE/POP glycerin ether, etc.); tetra POE/tetra POP ethylenediamine condensates (for example, Tetronic, etc.); POE castor oil hardened castor oil derivatives (for example, POE castor oil, POE hardened castor oil, POE hardened castor oil monoisostearate, POE hardened castor oil triisostearate, POE hardened castor oil monopyroglutamate monoisostearate diester, POE hardened castor oil maleate, etc.); POE bees wax/lanolin derivatives (for example, POE sorbitol bees wax, etc.); alkanolamides (for example, coconut oil fatty acid diethanolamide, coconut oil fatty acid monoethanolamide, lauric acid monoethanolamide, fatty acid isopropanol amide, etc.); POE propylene glycol fatty acid esters; POE alkylamines; POE fatty acid amides; sucrose fatty acid esters; alkylethoxydimethylamine oxides; trioleyl phosphate; and the like.

Examples of the amphoteric surfactant include lecithin, amidopropyl betaines (for example, coconut oil fatty acid amidopropyl betaine, lauric acid amidopropyl betaine, myristic acid amidopropyl betaine, palm kernel oil fatty acid amidopropyl betaine, etc.); amidosulfobetaines (for example, amidepropyl hydroxysulfobetaine laurate, etc.); amidoamine oxides (lauric acid amidopropyldimethylamine oxide, etc.); carbobetaines (for example, hydroxyalkyl (C12-14) hydroxyethylmethylglycine, etc.); and the like.

Among the surfactants used in the step (d) or (d'), sodium caseinate which is an anionic surfactant is preferable because it is particularly easily cultured and emulsified In the case where a surfactant is used as an emulsion in the emulsification step, the pH of the emulsion is preferably in the range of 7 to 11, in view of easily emulsifying the fat. The pH of the emulsion can be adjusted by adding an alkali. Therefore, in preparing the emulsion, it is preferable to add an alkali together with the surfactant.

The alkali that can be used is not particularly limited as long as it can adjust the pH of the emulsion to 7 to 11. Examples thereof include alkali metal hydroxides (e.g. sodium hydroxide, potassium hydroxide, lithium hydroxide, etc.); alkali metal carbonates (e.g. sodium carbonate, potassium carbonate, etc.); alkali metal hydrogen carbonates (e.g. sodium bicarbonate, potassium bicarbonate, etc.); alkali metal salts of organic acids (e.g. sodium acetate, potassium acetate, etc.); alkali metal borates (e.g. borax, etc.); alkali metal phosphates (e.g. trisodium phosphate, sodium hydrogen phosphate, disodium hydrogen phosphate 12 hydrate, disodium hydrogen phosphate, tripotassium phosphate, dipotassium hydrogen phosphate, etc.); alkaline earth metal hydroxides (e.g. barium hydroxide, etc.); ammonia water; and the like. Among them, sodium hydroxide, sodium carbonate, potassium hydroxide, and lithium hydroxide are preferable, and sodium hydroxide is particularly preferable in terms of industrial production and price. When protein is used in combination, disodium hydrogen phosphate is preferable because emulsification can be stabilized.

The preparation of the emulsion in the case of using the surfactant as an emulsion in the emulsification step (d) or (d') will be specifically described. When the emulsion is added to the fat obtained in the step (a), or when the fat obtained in the step (a) is added to the emulsion, the temperature of the emulsion and the fat are desirably the melting point of the fat or higher. It is preferable to adjust the temperature to 30 to 80° C. from the viewpoint of suppressing the decomposition of the surfactant and facilitating the emulsification.

The content of each of the surfactant to be added to the fat obtained in the step (a) will be described. In the case where the surfactant is used as an emulsion, the concentration of the fat obtained in the step (a) is preferably 40 to 70% by weight with respect to water, from the viewpoint of easily culturing. The concentration of the surfactant with respect to the fat obtained in the step (a) is preferably 0.01 to 1 part by weight, because a good emulsified state is likely to be obtained.

(Microbially Produced Plastic)

The microbially produced plastic manufactured by the above-mentioned manufacturing method is not particularly limited as long as it is a plastic composition containing a microbially produced plastic, but from the viewpoint of excellent biodegradability, the microbially produced plastic is preferably a polyhydroxyalkanoate (hereinafter sometimes referred to as PHA) represented by the following general formula (1):

$$[-CHR-CH_2-CO-O-] \tag{1}$$

(wherein R is an alkyl group represented by $C_nH_{2n+1}$ and n is an integer of 1 to 15).

The PHA may be a homopolymer having a PHA unit structure or a copolymer of two or more kinds thereof. For example, poly(3-hydroxybutyrate) (PHB), poly(3-hydroxybutyrate-co-3-hydroxyvalerate) (PHBV), [poly(3-hydroxybutyrate-co-3-hydroxyvalerate-co-3-hydroxyhexanoate) (P3HB3HV3HH), poly(3-hydroxybutyrate-co-3-hydroxyhexanoate) (PHBH), poly(3-hydroxybutyrate-co-4-hydroxybutyrate) (P3HB4HB), poly(3-hydroxybutyrate-co-3-hydroxyoctanoate), poly(3-hydroxybutyrate-co-3-hydroxyoctadecanoate), and the like are preferable from the viewpoint of easiness in industrial production. Among these, PHB, PHBV, P3HB3HV3HH, PHBH, and P3HB4HB are particularly preferable from the viewpoint of excellent balance of characteristics such as mechanical properties and biodegradability.

From the viewpoint of the balance between flexibility and strength, the average composition ratio of the repeating units of the microbially produced PHA is preferably such that the composition ratio of poly(3-hydroxybutyrate) is 80 mol % to 99 mol %, more preferably 85 mol % to 97 mol %. When the composition ratio of poly(3-hydroxybutyrate) is less than 80 mol %, the rigidity tends to be insufficient, and when the composition ratio of poly(3-hydroxybutyrate) is more than 99 mol %, the flexibility tends to be insufficient.

The ratio of each monomer which is a repeating unit in the PHA copolymer plastic can be measured by gas chromatography as follows. A mixed solution (2 ml) of sulfuric acid/methanol (15/85 (weight ratio)) and 2 ml of chloroform are added to about 20 mg of dry PHA, and the container is sealed tightly and heated at 100° C. for 140 minutes to obtain a methyl ester of PHA decomposition product. After cooling, 1.5 g of sodium bicarbonate was added little by little to neutralize the methyl ester, and leave it until generation of carbon dioxide stops. After addition of 4 ml of diisopropyl ether, followed by thoroughly mixing, the composition of the monomer unit of the PHA decomposition product in the supernatant is analyzed by capillary gas chromatography to determine the ratio of each monomer in the copolymer plastic.

"GC-17A" manufactured by Shimadzu Corporation is used as the gas chromatograph, and "NEUTRABOND-1" (column length: 25 m, column inner diameter: 0.25 mm, liquid film thickness: 0.4 μm) manufactured by GL Sciences Inc. is used as the capillary column. Helium is used as the carrier gas, the column inlet pressure is set to 100 kPa, and 1 μl of the sample is injected. As for the temperature condition, the temperature is raised from the initial temperature of 100° C. to 200° C. at a rate of 8° C./min and further raised to 200° C. to 290° C. at a rate of 30° C./min.

Since the microbially produced plastic manufactured by the manufacturing method of the present invention has low odor and low coloration, such plastic can be suitably used in the fields of agriculture, fishery, forestry, horticulture, medicine, sanitary goods, food industry, clothing, non-clothing, packaging, automobiles, and building materials, as well as in the other fields. The microbially produced plastic can be particularly suitably used in medical and hygienic fields such as biocompatible plastics such as drug carriers.

EXAMPLES

Next, the present invention will be described more specifically with reference to the following examples, but the present invention is not limited to these examples.

<Measurement of Color Tone (Absorbance)>

The color tone of the fat was measured as follows. The fat was heated to a temperature higher than the melting point of the fat, and the resulting fat in a state of being sufficiently melted was set in a measuring cell. Then, the absorbance at a wavelength of 450 nm was measured with an absorbance meter "UV-1700" (manufactured by Shimadzu Corporation) to evaluate the color tone. For the fat containing hydrogen peroxide and having been heat-treated, the fat in the oil layer portion obtained by leaving the fat to stand was collected, and the color tone (absorbance) of the collected fat was measured. Incidentally, the fat having a high absorbance indicates strong coloration.

<Measurement of Color Tone (HPLC Analysis)>

Measurement of color tone (HPLC analysis) was carried out as follows. Methanol (3 ml) was added to 0.5 g of PHA dry powder and the mixture was treated with ultrasonic waves for 30 minutes to extract the causative substance of coloration, which was filtered with a 0.45 μm PTFE membrane filter, and subjected to HPLC analysis using "Prominence" (manufactured by Shimadzu Corporation). From the chart of the result of HPLC analysis, the degree of color tone was evaluated by calculating the area of the peak of ubiquinone-8 which is the causative substance of coloration in PHA. A material containing a large amount of ubiquinone-8 indicates strong coloration.

<Sensory Evaluation of Color Tone>

Sensory evaluation of color tone of the culturing liquid immediately after the completion of the culture was carried out by 10 evaluators who judge the color tone. A case where 6 or more evaluators judged the color tone to be white or cream color was evaluated as Good, and a case where 6 or more evaluators judged the color tone to be obviously colored in yellow or brown color was evaluated as Poor. In addition, in the sensory evaluation of color tone of dry PHA, 50 g of dry PHA was weighed in a screw tube and evaluated by the same method as in the case of the culturing liquid.

<Measurement of Hue (YI Value)>

The measurement of hue (YI value) was carried out as follows. A press sheet of PHA was prepared and its YI value was measured. The press sheet of PHA was prepared by a method which includes sandwiching 3.0 g of dried PHA between metal plates of 15 cm square; further inserting a metal plate having a thickness of 0.5 mm into the four corners of the metal plate; setting the metal plate to a small experimental press machine (H-15 type, manufactured by Takabayashi Rika Co., Ltd.); heating the PHA at 160° C. for 7 minutes; pressing the PHA while heating at about 5 Mps for 2 minutes; and leaving the PHA to stand at room temperature for curing. The YI value was measured by placing a press sheet on a 30-mm measuring plate and placing a white standard plate thereon using a color difference meter "SE-2000" (manufactured by Nippon Denshoku Industries Co., Ltd.).

<Sensory Evaluation of Odor>

Sensory evaluation of odor of the fat was carried out by weighing 50 ml of fat in a screw tube and asking 10 evaluators to smell the odor. When 6 or more evaluators felt the odor was weak, the case was evaluated as Good, and when 6 or more evaluators felt the odor was strong, the case was evaluated as Poor. In the sensory evaluation of odor of dry PHA, 50 g of dry PHA was weighed in a screw tube and evaluated in the same method as in the case of the fat.

(Evaluation of Fats)

Measurement of color tone (absorbance) and sensory evaluation of odor were carried out for each of Palm Fatty Acid Distillate (hereinafter sometimes referred to as PFAD oil) which is a residual oil of a palm-derived fat, Empty Fruit Bunches pressed oil (hereinafter sometimes referred to as EFB pressed oil) which is a residual oil of a palm-derived fat, and dark oil which is a by-product mainly composed of fatty acids separated in the deacidification step in the process of producing an edible oil, and the results were shown in Table 1.

Preparation Example 1

PFAD oil (500 g) which is a residual oil of a palm-derived fat was placed in a 1 L separable flask, stirred with a first stage turbine blade, and heated to 95° C. Thereafter, 50 g of 30 wt % hydrogen peroxide water was added thereto and the mixture was reacted for 3.5 hours. Measurement of color tone (absorbance) and sensory evaluation of odor were carried out on the resulting treated fat, and the results were shown in Table 1.

Preparation Example 2

EFB pressed oil (500 g) which is a residual oil of a palm-derived fat was placed in a 1 L separable flask, stirred with a first stage turbine blade, and heated to 90° C. Thereafter, 50 g of 30 wt % hydrogen peroxide water was added thereto and the mixture was reacted for 1.5 hours. Measurement of color tone (absorbance) and sensory evaluation of odor were carried out on the resulting treated fat, and the results were shown in Table 1.

Preparation Example 3

Dark oil (500 g) which is a by-product mainly composed of fatty acids separated in the deacidification step in the process of producing an edible oil was placed in a 1 L separable flask, stirred with a first stage turbine blade, and heated to 70° C. Thereafter, 150 g of 30 wt % hydrogen peroxide water and 210 μl of 30 wt % sodium hydroxide were added thereto, and the mixture was reacted for 5 hours. Measurement of color tone (absorbance) and sensory evaluation of odor were carried out on the resulting treated fat, and the results were shown in Table 1.

Preparation Example 4

PFAD oil was treated in the same manner as in Preparation Example 1, except that the temperature of the PFAD oil was raised to 120° C. instead of raising the temperature to 95° C. Measurement of color tone (absorbance) and sensory evaluation of odor were carried out on the resulting treated fat, and the results were shown in Table 1.

Preparation Example 5

An emulsion was prepared by mixing 0.945 g of disodium hydrogen phosphate and 0.65 g of sodium caseinate in 70 g of water and stirring them until homogeneous at room temperature.

same document to obtain a cell culturing liquid including cellular bodies containing PHA. Details are given below. As the carbon source, 70 parts by weight of the emulsion prepared in Preparation Example 5 was added to and mixed with 130 parts by weight of the treated fat prepared in Preparation Example 1 was used.

The composition of the seed culture medium was 1% (w/v) Meat-extract, 1% (w/v) Bacto-Tryptone, 0.2% (w/v) Yeast-extract, 0.9% (w/v) $Na_2HPO_4.12H_2O$, and 0.15% (w/v) $KH_2PO_4$, (pH 6.8). The composition of the preculture medium was 1.1% (w/v) $Na_2HPO_4.12H_2O$, 0.19% (w/v) $KH_2PO_4$, 1.29% (w/v) $(NH_4)_2SO_4$, 0.1% (w/v) $MgSO_4.7H_2O$, 2.5% (w/v) palm double oleic oil, and 0.5% (v/v) trace metal salt solution (1.6% (w/v) $FeCl_3.6H_2O$, 1% (w/v) $CaCl_2.2H_2O$, 0.02% (w/v) $CoCl_2.6H_2O$, 0.016% (w/v) $CuSO_4.5H_2O$, and 0.012% (w/v) $NiCl_2.6H_2O$ were dissolved in 0.1 N hydrochloric acid).

The composition of the plastic production medium was 0.385% (w/v) $Na_2HPO_4.12H_2O$, 0.067% (w/v) $KH_2PO_4$, 0.291% (w/v) $(NH_4)_2SO_4$, 0.1% (w/v) $MgSO_4.7H_2O$, 0.5% (v/v) trace metal salt solution (1.6% (w/v) $FeCl_3.6H_2O$, 1% (w/v) $CaCl_2.2H_2O$, 0.02% (w/v) $CoCl_2.6H_2O$, 0.016% (w/v) $CuSO_4.5H_2O$, and 0.012% (w/v) $NiCl_2.6H_2O$ were dissolved in 0.1 N hydrochloric acid), and 0.05% (w/v) BIO-SPUREX 200K (anti-foaming agent: manufactured by Cognis Japan Ltd.). The treated fat prepared in Preparation Example 1 was used as a single carbon source, and the fat was subjected to fed-batch culture so that the specific substrate feed rate would be, throughout the culture, 0.08 to 0.1 (g fat)×(g net dry cell weight)$^{-1}$×(h)$^{-1}$.

A glycerol stock of KNK-005 strain (50 μL) was inoculated into the seed culture medium (10 mL) and seed-cultured for 24 hours to obtain a seed culture. Then, 1.0% (v/v) of the seed culture was inoculated into a 3 L jar fermenter (MDL-300 type, manufactured by B. R. MARUBISHI Co., Ltd.) containing 1.8 L of the preculture medium. The jar fermenter was operated under conditions of a culture temperature of 33° C., a stirring speed of 500 rpm, and a ventilation volume of 1.8 L/min to perform preculture for 28 hours while pH was controlled to fall within the range from 6.7 to 6.8. The pH control was performed using a 7% aqueous ammonium hydroxide solution.

TABLE 1

|  | PFAD oil | | | EFB pressed oil | | Dark oil | |
| --- | --- | --- | --- | --- | --- | --- | --- |
|  | Preparation example 1 | Preparation example 4 | No treatment | Preparation example 2 | No treatment | Preparation example 3 | No treatment |
| Treatment temperature of fat | 95° C. | 120° C. |  | 90° C. |  | 70° C. |  |
| Color tone (Absorbance at 450 nm) | 0.68 | 0.45 | 1.95 | 0.76 | 3.21 | 1.06 | Unmeasurable |
| Odor (Sensory evaluation) | Good | Good | Poor | Good | Poor | Good | Poor |

The results of Preparation Examples 1 to 4 reveals that the color tone and odor of the fat have been reduced by the heat treatment step (a).

Example 1

For culturing and refining, *Ralstonia eutropha* KNK-005 strain disclosed in paragraph [0049] of PCT International Publication No. 2008/010296 was cultured according to the same process disclosed in paragraphs [0050] to [0053] of the Then, 5.0% (v/v) of the preculturing liquid was inoculated into a 10 L jar fermenter (MDS-1000 type, manufactured by B. R MARUBISHI Co., Ltd.) containing 6 L of the production medium. The jar fermenter was operated under conditions of a culture temperature of 28° C., a stirring speed of 400 rpm, and 3.6 L/min, and pH was controlled to fall within the range from 6.7 to 6.8. The pH control was performed using a 7% aqueous ammonium hydroxide solution. As a carbon source, the treated fat prepared in Preparation Example 1 was used. Culture was performed for 64 hours.

The obtained cell culturing liquid was sterilized at 60° C. for 30 minutes. After completion of the cultivation, the cells were collected by centrifugation, and subjected to enzymatic treatment and high-pressure crushing at a pressure of 450 to 550 kgf/cm$^2$ with a high-pressure crusher (High Pressure Homogenizer Model PA2K model, manufactured by Niro Soavi).

After centrifugation of the crushed liquid after high-pressure crushing, the supernatant was eliminated, and the collected PHA solution was agglomerated and dried. The obtained PHA dry powder was subjected to odor sensory evaluation, hue (YI value) measurement, color tone (HPLC analysis) measurement, and the results were shown in Table 2.

Example 2

A PHA dry powder was obtained in the same manner as in Example 1, except that the emulsion obtained using the treated fat prepared in Preparation Example 4 was used as the carbon source used in the medium instead of the treated fat prepared in Preparation Example 1. The obtained PHA dry powder was subjected to odor sensory evaluation, color (YI value) measurement, and color tone (HPLC analysis) measurement, and the results were shown in Table 2.

Comparative Example 1

A PHA dry powder was obtained in the same manner as in Example 1, except that PFAD oil of Preparation Example 1, which was not treated, was used as the carbon source used for the medium. The obtained PHA dry powder was subjected to odor sensory evaluation, hue (YI value) measurement, and color tone (HPLC analysis) measurement, and the results were shown in Table 2.

TABLE 2

| | Example 1 | Example 2 | Comparative example 1 |
|---|---|---|---|
| Odor (Sensory evaluation) | Good | Good | Poor |
| Color tone (Peak area by HPLC analysis) | 481 | — | 1758 |
| Hue (YI value) | 11.1 | 14.1 | 18.0 |

When the PHA of Example 1 produced by the manufacturing method of the present invention is compared with the PHA of Comparative Example 1 prepared by using the fat not treated with hydrogen peroxide water, the peak area of ubiquinone-8 as measured by color tone (HPLC analysis) was small, that is, the content of ubiquinone-8 as an impurity was extremely small and the YI value was also small, that is, the coloration was low. In addition, when the PHA of Example 2, which was less colored than the fat treated at 95° C., produced by using the fat that was heat-treated at 120° C. was compared with the PHA of Example 1, the peak area of ubiquinone-8 as measured by HPLC analysis for the color tone was somewhat higher than that of Example 1, but the content of ubiquinone-8 was lower than that in the PHA of Comparative Example 1, because of which the coloration was also low.

Example 3

The culture was carried out in the same manner as in Example 1, except that the emulsion obtained by using the treated fat prepared in Preparation Example 2 was used as the carbon source for use in the medium, instead of the treated fat prepared in Preparation Example 1. Sensory evaluation of color tone was performed on the obtained cell culturing liquid, and the results were shown in Table 3.

Comparative Example 2

The culture was carried out in the same manner as in Example 3, except that the non-treated EFB pressed oil of Preparation Example 2 was used as the carbon source for use in the medium. Sensory evaluation of color tone was performed on the obtained cell culturing liquid, and the results were shown in Table 3.

Example 4

A PHA dry powder was obtained in the same manner as in Example 1, except that the emulsion obtained by using the treated fat prepared in Preparation Example 3 was used as the carbon source for use in the medium, instead of the treated fat prepared in Preparation Example 1. Sensory evaluation of color tone on each of the obtained cell culturing liquid and the PHA dry powder was performed, and the results were shown in Table 3.

Comparative Example 3

A PHA dry powder was obtained in the same manner as in Example 4, except that the non-treated dark oil of Preparation Example 3 was used as the carbon source for use in the medium. Sensory evaluation of color tone on each of the obtained cell culturing liquid and the PHA dry powder was performed, and the results were shown in Table 3.

TABLE 3

| | Example 3 | Comparative example 2 | Example 4 | Comparative example 3 |
|---|---|---|---|---|
| Fat | Preparation example 2 | No treatment | Preparation example 3 | No treatment |
| Color tone of culturing liquid (Sensory evaluation) | Good | Poor | Good | Poor |
| Dry PHA after refining Color tone (Sensory evaluation) | — | — | Good | Poor |

The coloring of the culturing liquids of Examples 3 and 4 containing PHA produced by the manufacturing method of the present invention was obviously less than the coloring of the culturing liquids of Comparative Examples 2 and 3 containing PHA produced by using the fat that was not treated with hydrogen peroxide water. Further, in Example 4 in which the PHA dry powder was obtained, the coloring was clearly less than in Comparative Example 3.

As shown in Tables 2 and 3, by treating the fat with hydrogen peroxide, an effect of reducing color tone and odor was observed in both the culturing liquid and the dry PHA.

The invention claimed is:

1. A method of manufacturing a microbially produced plastic, the method comprising:
    mixing fat and hydrogen peroxide and simultaneously applying heat treatment to a mixture of the fat and hydrogen peroxide, wherein the heat treatment is performed at a temperature of form 50° C. to 150° C., and
    culturing microbes in a culturing liquid comprising the fat that has been subjected to the heat treatment in the mixing, wherein the microbially produced plastic is a polyhydroxyalkanoate.

2. The method according to claim 1, wherein the fat comprises a plant-derived fat.

3. The method of manufacturing a microbially produced plastic according to claim 1, wherein the fat contains a residual oil.

4. The method of manufacturing a microbially produced plastic according to claim 1, wherein the fat contains a palm-derived fat.

5. The method of manufacturing a microbially produced plastic according to claim 1, wherein the fat contains a palm-derived residual oil.

6. The method according to claim 1, further comprising:
   taking out a plastic component from the microbes cultured in the culturing.

7. The method according to claim 1, further comprising:
   emulsifying the fat by adding a surfactant to the fat that has been heat-treated in the mixing and simultaneously applying heat treatment.

8. The method according to claim 1, further comprising:
   emulsifying the fat by adding a surfactant and sodium hydroxide to the fat that has been heat-treated in the mixing and simultaneously applying heat treatment.

9. The method according to claim 7, wherein the emulsifying of the fat by adding a surfactant is performed before the culturing.

10. The method according to claim 8, wherein the emulsifying of the fat by adding a surfactant and sodium hydroxide is performed before the culturing.

* * * * *